(12) United States Patent
Ershov et al.

(10) Patent No.: US 8,847,769 B2
(45) Date of Patent: Sep. 30, 2014

(54) SIGNAL DETECTING DEVICE FOR DETECTING A DIFFERENCE SIGNAL FOR AN ELECTRICAL MEASUREMENT OF A VITAL PARAMETER OF A LIVING BEING

(75) Inventors: Sergey Ershov, Erlangen (DE);
Hans-Joachim Moersdorf, Fuerth (DE);
Ruslan Rybalko, Nuremberg (DE);
Robert Couronne, Erlangen (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 551 days.

(21) Appl. No.: 12/913,566

(22) Filed: Oct. 27, 2010

(65) Prior Publication Data
US 2011/0125002 A1    May 26, 2011

(30) Foreign Application Priority Data
Oct. 27, 2009    (DE) .......................... 10 2009 050755

(51) Int. Cl.
| G08B 23/00 | (2006.01) |
| A61B 5/18 | (2006.01) |
| A61B 5/0428 | (2006.01) |
| A61B 5/04 | (2006.01) |
| A61B 5/0245 | (2006.01) |

(52) U.S. Cl.
CPC ................. *A61B 5/18* (2013.01); *A61B 5/0428* (2013.01); *A61B 5/0245* (2013.01)
USPC .......................................... 340/575; 600/372

(58) Field of Classification Search
USPC ............ 74/484 R, 552, 558, 558.5; 180/272;
340/426.31, 439, 573.1, 575–576;
600/300–301, 372, 382, 384, 393,
600/508–509, 544–547
See application file for complete search history.

(56) References Cited

U.S. PATENT DOCUMENTS

| 3,971,366 | A | * | 7/1976 | Motoyama ..................... 600/384 |
| 4,577,639 | A | | 3/1986 | Simon et al. |
| 5,184,620 | A | * | 2/1993 | Cudahy et al. ................ 600/382 |
| 5,503,158 | A | * | 4/1996 | Coppock et al. .............. 600/508 |
| 5,715,821 | A | * | 2/1998 | Faupel .......................... 600/302 |
| 7,187,292 | B2 | * | 3/2007 | Hayashi et al. ............... 340/576 |
| 2003/0073886 | A1 | | 4/2003 | Yanagidaira |
| 2004/0133082 | A1 | | 7/2004 | Abraham-Fuchs |
| 2005/0010121 | A1 | | 1/2005 | Ross et al. |
| 2005/0239075 | A1 | * | 10/2005 | Yanagidaira et al. ............. 435/6 |
| 2008/0238695 | A1 | | 10/2008 | Yanai et al. |
| 2008/0243013 | A1 | | 10/2008 | Yanai |
| 2009/0259137 | A1 | * | 10/2009 | Delic et al. .................... 600/545 |
| 2010/0041975 | A1 | * | 2/2010 | Chen et al. .................... 600/393 |

(Continued)

FOREIGN PATENT DOCUMENTS

| DE | 10249415 | B3 | 3/2004 |
| DE | 102004036119 | | 2/2006 |

(Continued)

*Primary Examiner* — Linda Dvorak
*Assistant Examiner* — Brian M Antiskay
(74) *Attorney, Agent, or Firm* — Michael A. Glenn; Perkins Coie LLP (57) ABSTRACT

What is described are a signal detecting device for detecting a vital parameter of a living being, having a plurality of electrodes and an electrode selecting device for selecting a pair of electrodes from the plurality of electrodes such that a difference signal suitable for measuring the vital parameter is derivable, an electrode arrangement and a method.

19 Claims, 9 Drawing Sheets

(56) References Cited

FOREIGN PATENT DOCUMENTS

| | | |
|---|---|---|
| DE | 102005007963 | 8/2006 |
| DE | 60214312 | 9/2007 |
| GB | 2390460 | 1/2004 |
| JP | 2009/142575 | 7/2009 |
| WO | WO 98/25520 | 6/1998 |
| WO | WO02/096694 | 12/2002 |
| WO | WO 2008/005478 | 1/2008 |

* cited by examiner

SIGNAL DETECTING DEVICE FOR DETECTING A DIFFERENCE SIGNAL FOR AN ELECTRICAL MEASUREMENT OF A VITAL PARAMETER OF A LIVING BEING

CROSS-REFERENCE TO RELATED APPLICATION

This application claims priority from German Patent Application No. 10 2009 050 755.8, which was filed on Oct. 27, 2009, and is incorporated herein by reference in its entirety.

BACKGROUND OF THE INVENTION

The present invention relates to a signal detecting device for detecting a difference signal for an electrical measurement of a vital parameter of a living being, for example an ECG measurement, to an electrode arrangement as may exemplarily be arranged in a motorcar (MC), and to a method.

The heart, being one of the most important organs of the human organism, represents a broad basis for diagnosing most different diseases in medicine. Electrical potentials form on the body's surface caused by the three-dimensional propagation of the excitation in the heart. Detecting temporal changes of potential differences between defined positions on the body's surface is referred to as electrocardiography. The recording of the potential lines resulting is referred to as electrocardiogram, abbreviated as ECG.

The electrical potentials are, for detecting the ECG, fed to high-resistance amplifiers via electrodes on the body's surface. The potentials to be recorded are of an amplitude of 50 µV-5 mV and comprise frequency components in the range from 0.1 to 150 Hz. The ECG is recorded via electrodes on the thorax or arms as a standard. Depending on the number of channels to be recorded, the number of electrodes typically varies between three and ten.

At present, there are various forms of ECGs, a particular difference here being the application time. Short-term ECGs serve for quickly diagnosing the heart's function, whereas prolonged ECGs are able to record the heart's function over a longer period of time. In contrast to body function monitoring devices which are also available for end users, such as, for example, pulse watches, electrocardiographs for recording ECGs are frequently operated by physicians only due to their complexity. Here, electrodes via which the potential differences can then be measured are applied to the body of a human being following a certain principle. The individual electrodes applied to the body are connected via cables to evaluating means which detect the changes in potential differences over time.

Several systems are known for increasing traffic safety, which allow estimating the mental and physical state of the driver on the basis of his vital parameters measured in the vehicle. Conclusions from such systems may be applied in the following fields: diagnosis and/or therapy support, recognizing emotions, concentration of the driver, tiredness and sleepiness, and quantization of vegetative stress levels.

Some systems also offer a way of acting on the control units of the automobile depending on the state of the driver established. These systems are usually referred to as: health monitoring systems, driver assistance systems, body state measuring means, vehicle safety devices and therapeutic systems.

DE 102 49 415 B3 describes a system for supporting the diagnosis, therapy and/or preventive treatment of a person in the vehicle. Sensory monitoring of the patient here means measuring weight and respiratory rate.

WO 98/25520 describes a security device for detecting, warning and preventing decreasing concentration of the vehicle driver and for warning or preventing sleepiness. The document cited also suggests implementing an emotion detector system. The physical measuring quantities for this are heart rate, heart rate variability and body temperature which are sampled using electrodes on the steering wheel, and pulse which is sampled using pulse measuring devices on the surface of the steering wheel.

WO 02/096694 A1 describes a method and means for characterizing the state of the driver of a motorcar, the control units of the motorcar being influenced using the results established. The concept in accordance with the publication cited takes several physiological state variables, such as, for example, ECG, heart rate, EEG, blood pressure, skin temperature, skin conductivity, eyelid frequency, gripping force and movements of the driver in his seat, into account.

DE 10 2005 007 963 A1 describes a method and means for quantizing a vegetative stress level. The document cited describes determining the vegetative stress level also under automobile conditions by means of heart rate monitoring. Recording the heart rate may in this case be done using sensors or sensor fields which are integrated in the operating devices—steering wheel, gear shift lever—of a vehicle.

DE 60124971 T2 describes a health monitoring system. The system suggested may, among other things, be used for monitoring the person in the vehicle. The measuring quantities here are heart rate data recorded by plate electrodes on the steering wheel, secretion of sweat recorded by sweat sensors (term used by the inventor) on the steering wheel, and the video image of a camera. The health monitoring system is optimized for monitoring several persons at the same time.

GB 2 390 460 A describes a tiredness alerter which determines a driver's tiredness level using his body temperature, pulse rate, blood pressure and oxygen saturation in the blood.

DE 10 2004 036 119 B4 describes a driver assistance system for recognizing tiredness and evaluating the attentiveness of a driver using his pulse frequency. The sensors for detecting the pulse frequency are, in accordance with the document cited, to be integrated in the steering wheel, gear selecting lever or seat.

DE 602 14 312 T2 describes an apparatus for measuring the state of a driver's body. The following vital parameters are detected here: pulse, sweat secretion, skin resistance, respiration, heart rate and heart rate variability. Embodiments thereof are the following variations:
a) body state measuring means for determining whether the operator is in a "steady state",
b) body state measuring means and interaction thereof with a navigation system, and
c) body state measuring means and interaction thereof with a music system.

One disadvantage of many diagnostic methods for the cardiovascular system when being used under automobile conditions, but also in diagnostics, for example when seeing a physician, is that they are either of invasive character or that application parts thereof (electrodes and leads thereof) have to be applied to the body before measuring and be connected to signal evaluating electronics.

Most known systems for monitoring drivers by means of vital sensor technology (such as, for example, pulse measurements or ECG) are only described too generally and ignore important aspects such as: signal quality, coverage of the passenger area with sensors, probability and frequency of sensor contacts by the driver, diverting the driver by the interaction with the measuring system and potentially resulting impairment of driving safety, and build-up time of the sensors, i.e. how fast the sensors are able to provide valid data after being touched.

Some health assistance systems promise the possibility of diagnosing or diagnosis support, preventive treatment or even therapy support when being used in automobiles. However, up to now there are no systems known on the market which are really able to record vital data in automobiles for diagnostics and therapy support with the precision needed. This may be explained by the challenging fringe conditions and the lack of acceptance on the part of the driver (sensor on the body) in the automobile environment.

Possible systems for detecting a vital parameter of a living being, such as, for example, an ECG, may be provided with a plurality of electrodes, the plurality of electrodes generating difference signals from which an ECG can be derived. This means that the quality of the ECG is strongly dependent on the signal strength of the electrodes.

SUMMARY

According to an embodiment, a signal detecting device for determining a difference signal for an electrical measurement of a vital parameter of a living being may have: a plurality of electrodes configured to contact the living being and provide electrode signals; and an electrode selecting device configured to select a pair of electrodes for determining the difference signal from the plurality of electrodes based on the electrode signals so that a difference signal suitable for measuring the vital parameter is derivable from the electrode signals of the selected electrodes.

According to another embodiment, an electrode arrangement may have: a plurality of electrodes; wherein the plurality of electrodes are arranged in a motorcar (MC) so as to contact an MC user; wherein at least a first electrode from the plurality of electrodes is arranged at or in an operating element of the MC; and wherein at least a second electrode from the plurality of electrodes is arranged at or in a rest element of the MC.

According to still another embodiment, a method for determining a difference signal for an electrical measurement of a vital parameter of a living being using a plurality of electrode signals from a plurality of electrodes may have the steps of: a) detecting a plurality of electrode signals from the electrodes configured to contact the living being and provide electrode signals, b) selecting a pair of electrodes from the plurality of electrodes based on the electrode signals such that a difference signal suitable for measuring the vital parameter is derivable from the electrode signals of the selected electrodes; and c) deriving a difference signal suitable for measuring the vital parameter from the electrode signals of the selected pair of electrodes.

The central idea of the present invention is based on the finding that improved recording of a vital parameter of a living being is made possible when a signal detecting device is provided with a plurality of electrodes, typically more electrodes than are absolutely needed for providing a difference signal, and when an electrode selecting device of the signal detecting device is able to select, depending on the electrode signals, a pair of electrodes from the plurality of electrodes, in which a difference signal suitable for measuring the vital parameter are derivable, since a contact of differing quality or, in some electrodes, completely lacking contact between the electrodes and the living being does not result in an unusable measuring result, but rather in an automatic selection of suitable electrodes. Assuming that at least part of the plurality of electrodes do contact the living being, due to the selection of a pair of electrodes based on the electrode signals, a difference signal of sufficiently good signal quality is used for measuring the vital parameter.

Consequently, one advantage of the present invention is that redundancy of electrodes contacting the body results from the plurality of electrodes and that that pair of electrodes which have the most suitable difference signal for measuring the vital parameter may be selected by the electrode selecting device.

Additionally, the present invention provides an electrode arrangement comprising a plurality of electrodes, the plurality of electrodes being arranged in a motorcar so as to contact the user, wherein at least one of the electrodes is arranged in an operating element of the motorcar and at least one other electrode is arranged in a rest element of the motorcar.

Subsequently, operating element also means a control element, such as, for example, a steering wheel or gear shift lever, or a switching element, such as, for example, a rotary switch of a radio or an indicator lever.

A "motorcar" will subsequently also be referred to as "MC" in short.

This aspect of the present invention is based on the finding that, when driving, an MC user will typically not have his hands located on operating element of the MC or the steering wheel permanently. Knowing that, when driving, an MC user will frequently have one of his hands located on an operating element, such as, for example, the steering wheel or gear lever of the MC, and another hand located on a rest element, such as, for example, an armrest area of the MC, there will be increased contacting probability and thus improved continuous detection for the electrical measurement of a vital parameter of the MC user, caused by the integration of at least one electrode in a rest element of the MC.

Thus, another advantage of the present invention is that electrode signals may even be provided when an MC user does not have both hands located on an operating element, such as, for example, the steering wheel.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
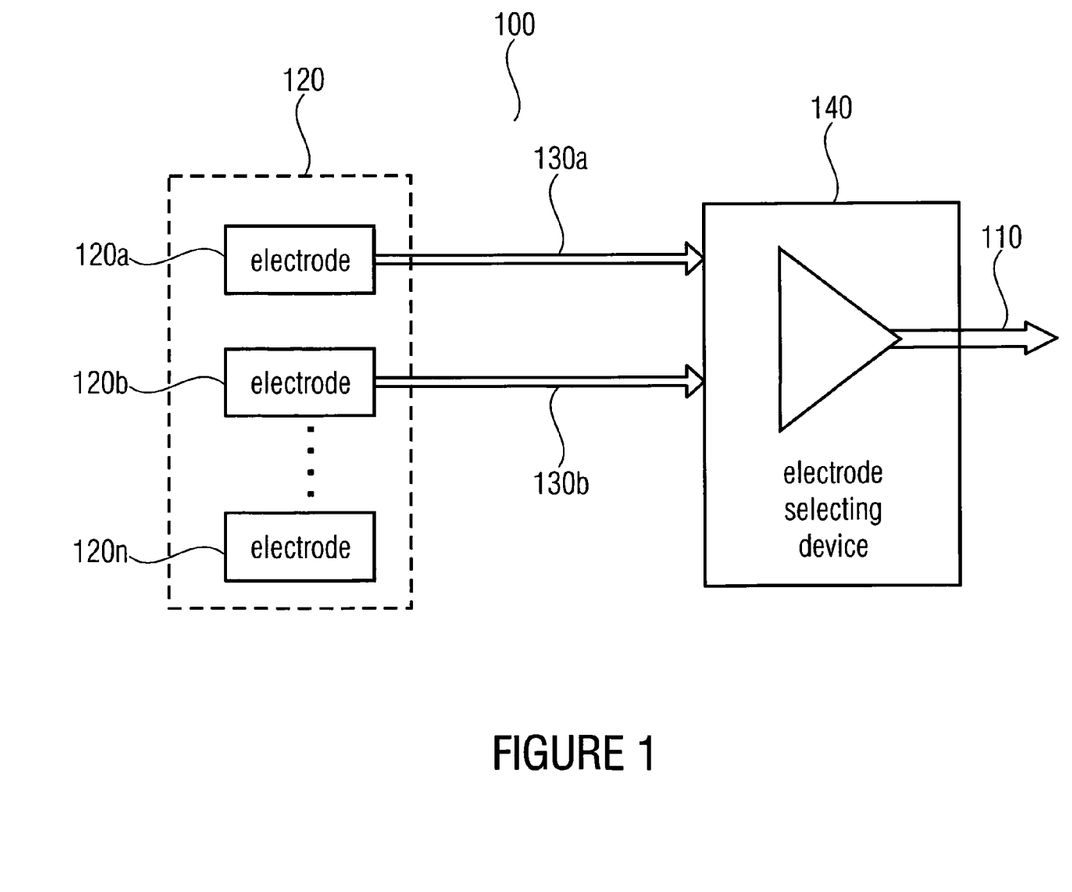
FIG. 1 shows a schematic illustration of a signal detecting device in accordance with a first embodiment of the present invention.

FIG. 1 shows a schematic illustration of a signal detecting device 100 in accordance with a first embodiment of the present invention. The signal detecting device 100 for detecting a difference signal 110 for an electrical measurement of a vital parameter of a living being includes a plurality 120 of electrodes 120a-120n and an electrode selecting device 140. The electrodes 120a-120n are connected to the electrode selecting device 140 so as to provide electrode signals 130 to the electrode selecting device 140.

Electrodes 120a-120n from the plurality of electrodes can contact the living being and provide electrode signals 130 to the electrode selecting device 140. Based on, for example, the strength (or amplitude) of the electrode signals 130 (or another characteristic feature of the electrode signals 130, like, for example, an intensity and characteristic signal shape or a characteristic frequency portion) of the individual electrodes 120a-120n, the electrode selecting device 140 can select one pair of electrodes 120a-120n which allow providing a difference signal 110 most suitable or a difference signal 110 of at least sufficient suitability for measuring the vital parameter, and deriving therefrom the difference signal 110 for measuring the vital parameter of the living being. By selecting the pair of electrodes 120a-120n based on the signal strength or the electrode signals 130, it can be ensured that the best difference signal 110 possible (or an at least sufficiently good one) will be used for measuring the vital parameter of the living being. Additionally, the electrode selecting device 140 is able to select, when the electrode signals 130 of the electrodes 120a-120n change (or when characteristic features thereof change), another pair of electrodes 120a-120n for generating the difference signal 110 which generate a better difference signal 110 than the previous pair of electrodes 120a-120n (or allows providing a better difference signal 110). The options for recording a difference signal 110 can be increased significantly by using several redundant electrodes 120a-120n. The electrodes 120a-120n here do not necessarily have to be mounted permanently to a living being, but may also be applied on areas which the living being touches (permanently or temporarily). Thus, the signal detecting device 100 and/or the plurality 120 of electrodes of the signal detecting device 100 may exemplarily be arranged in an MC.

Figure 2:
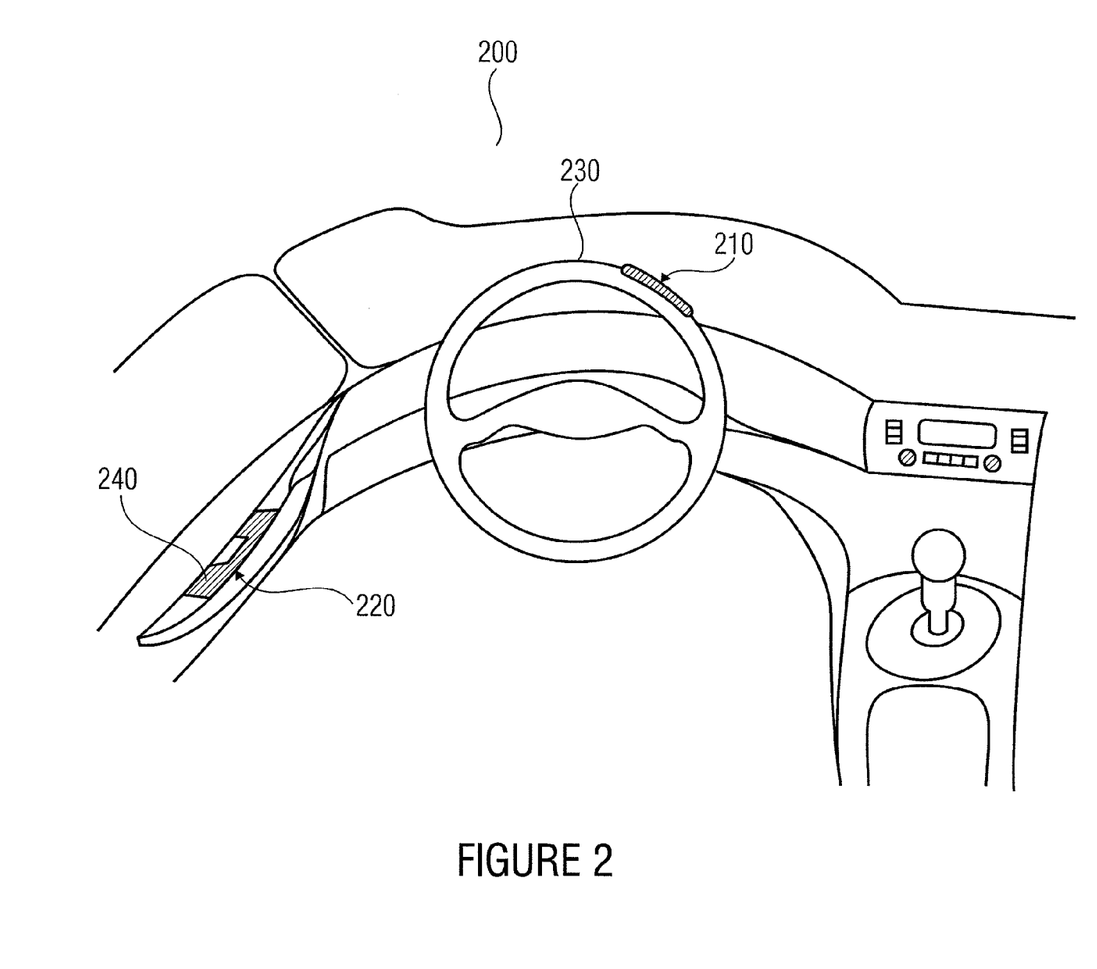
FIG. 2 shows a picture of an electrode arrangement in accordance with a second embodiment of the present invention.

FIG. 2 shows a picture of an electrode arrangement 200 in accordance with a second embodiment of the present invention. The electrode arrangement 200 is integrated in an MC, a first electrode 210 being applied in, at or on an operating element 230. A second electrode 220 is applied in, at or on a rest element 240 of the MC. The operating element 230 may exemplarily be a steering wheel of the MC, wherein the rest element 240 may exemplarily be an armrest area of the driver's door of the MC.

The first electrode 210 and the second electrode 220 are arranged in the MC such that they are able to contact the MC user (exemplarily when same is in a driving position). Exemplarily, the first electrode 210 may be arranged such that it contacts the right hand of the MC user and the second electrode 220 may be arranged such that it contacts the left hand of the MC user. The electrode arrangement 200 shown may thus be used to detect, for example, a difference signal for electrically measuring a vital parameter of the MC user, such as, for example, an ECG. A difference signal between the first electrode 210 and the second electrode 220 (exemplarily in the form of a difference signal describing a difference of the potentials applied to the electrodes) can be detected here, the difference signal resulting from potentials generated by the heartbeat of the living being.

It is additionally possible for additional electrodes to be arranged in or on the operating element 230 as well as in or on other operating elements or rest elements of the MC.

An electrode will subsequently also be referred to as a measuring electrode or contact electrode.

An MC user will subsequently be referred to as a driver in short.

Figure 3A:
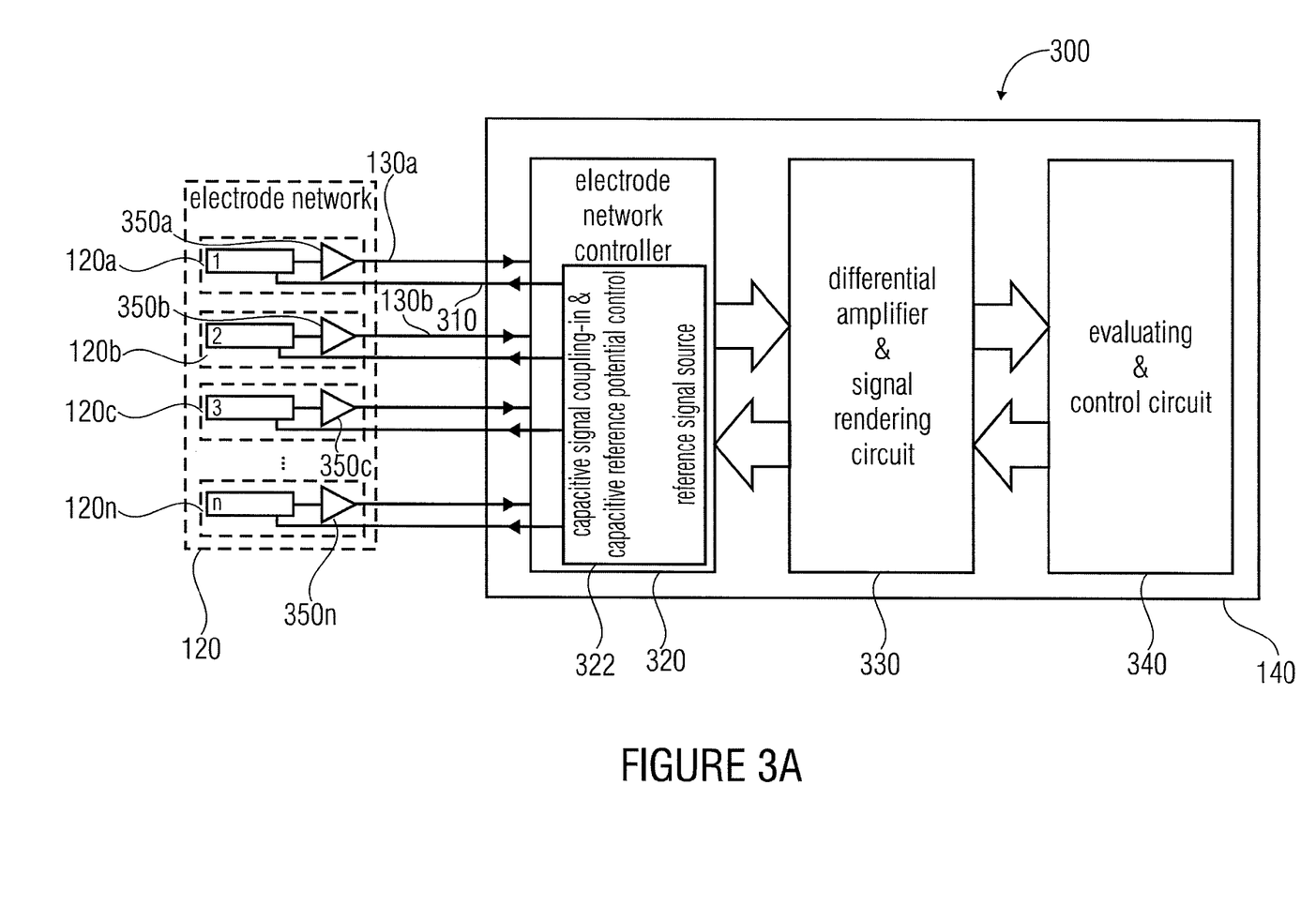
FIG. 3 shows a schematic illustration of a signal detecting device in accordance with a third embodiment of the present invention.

FIG. 3a shows a schematic illustration of a signal detecting device 300 in accordance with a third embodiment of the present invention. The signal detecting device 300 includes a plurality of electrodes 120a-120n or electrode network 120. The electrode network 120 includes at least a first electrode 120a, a second electrode 120b and a third electrode 120c. The electrode network 120 may include any number of additional electrodes 120a-120n. In addition, the signal detecting device 300 includes an electrode selecting device 140. The electrode selecting device 140 includes an electrode network controller 320, a differential amplifier and signal rendering circuit 330 and an evaluating and control circuit 340. The electrode network controller 320 includes means 322 for capacitive signal coupling-in and capacitive reference potential driving including a reference signal source. In other words, FIG. 3a shows an exemplary integration of the signal detecting device 300 or the system for detecting the ECG by means of a network 120 of the contact electrodes 120a-120n or capacitive electrodes 120a-120n including capacitive coupling-in of the signal and capacitive reference potential control 322. The electrodes 120a-120n each include a downstream amplifier 350a-350n. The electrodes 120a-120n are connected to the electrode network controller such that they can provide electrode signals 130a-130n to the electrode network controller 320. The means 322 of the electrode network controller 320 in turn can provide signals 310 to the electrodes 120a-120n. The ECG electrodes 120a-120n are, for example, integrated in the passenger area of an MC, as has exemplarily been described using FIG. 2. The circuit does not have a separate reference electrode for reference potential control and signal common-mode rejection.

The signals of the reference potential control (stabilizing the baseline) and signal common-mode rejection are fed to the MC user via the same measuring electrodes 120a-120n used for ECG sampling. A special circuit for capacitive coupling-in of the ECG measuring signal and capacitive feedback of the reference signal is provided for this at the input of the measuring system, such as, for example, means 322. Additionally, a reference signal 310 (a sinusoidal or modulated signal) is fed to the MC user or driver via the measuring electrodes 120a-120n for the purpose of electrode control (determining the electrodes 120a-120n contacting the MC user). The amplitude and frequency ranges of this reference signal 310 are in correspondence with the allowed threshold values for ECG measuring systems (such as, for example, patient leakage currents in accordance with ISO 60601). The reference signal 310 for electrode control is not coupled in at all measuring electrodes 120a-120n at the same time, but is step by step fed to one of the measuring electrodes 120a-120n after the other. This allows iteratively starting a search routine which determines other electrodes 120a-120n (for example different ones from the electrode where the reference signal 310 is currently coupled in) being in contact with the MC user and may at the same time provide information on whether the electrode where the reference signal 310 is coupled in is in sufficiently good contact to the MC user. When the search routine does not provide any results, i.e. when no electrode signal is determined at any electrode different from the source electrode (electrode where the reference signal 310 is coupled in) based on the reference signal 310, this means that there is no contact to the initial source electrode. In this case, the reference signal 310 is fed, for electrode control, to another measuring electrode 120a-120n as the source electrode. The electrode recognition routine will start searching for contact to electrodes 120a-120n in a predefined order in order for the search time to be minimized and the electrode recognition routine to become a systematic process. The order of feeding the reference signal 310 results from the probability with which the corresponding electrode 120a-120n is touched by the driver (contacting probability). A left (ECG) electrode 120a-120n at the steering wheel of the MC, for example, is recommended as the starting point of the electrode recognition routine.

The search routine operates as follows: the pre-amplified signals 130a-130n from individual electrodes 120a-120n are detected using the comparator measuring system installed in the electrode network controller 322 and compared to an initial reference signal (or in some embodiments even several initial reference signals) which may exhibit different potential signal shapes, exemplarily be sinusoidal or modulated. This means that the electrodes 120a-120n which are in contact with the driver are determined and the electrodes 120a-120n of the best signal quality are selected on the basis of the signal strength of the electrode signals 130a-130n. After that, the selected electrodes 120a-120n are fed to the differential amplifier 330 via multiplexer matrices of different logical algorithms. Finally, the pair of (ECG) electrodes 120a-120n which have the best contact to the MC user and provide the best difference signal 110 are selected for detecting the ECG. The reference signal 310 used for electrode detection (contact to the driver, signal quality) will later on be filtered from the useful signal.

Figure 3B:
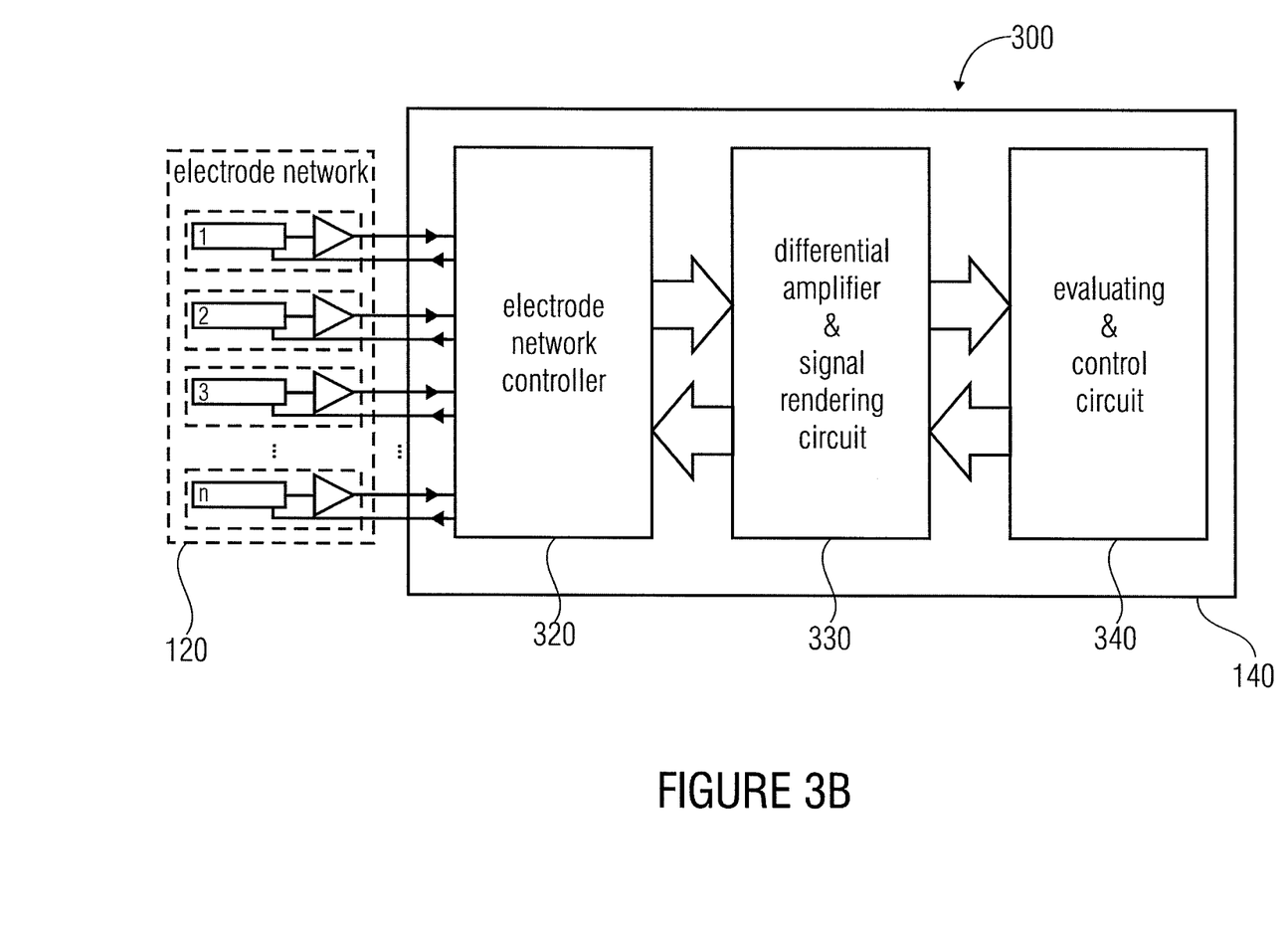

FIG. 3b shows the signal detecting device 300 without the means 322 for capacitive signal coupling-in and capacitive reference potential control including a reference signal source.

The measuring device or signal detecting device 300 in FIGS. 3a and 3b thus basically consists of the "network" of switchable active electrodes 120a-120n, the electrode network controller 320, the differential instrumentation amplifier and the signal rendering circuit 330 and the evaluating and control circuit 340. The signal detecting device 300 shown may exemplarily be integrated in an MC to continuously record the ECG of a driver while driving, for example. The signal detecting device 300 measures the difference of the electrical potentials caused by heart activity on the body's surface of the driver or MC user via the electrodes 120a-120n. In a first step, electrodes 120a-120n which are in electrical or capacitively coupled contact to the driver are automatically recognized and enabled by schematic (electrode network controller 320) and algorithmic methods. Electrodes 120a-120n not currently used (electrodes without contact to the MC user) are switched off, but nevertheless continuously monitored as to their signal strength and quality in order to be able to enable the best electrode configuration (the pair of electrodes providing the best difference signal or an at least sufficiently good one) when needed. At least two electrodes 120a-120n may be enabled for the measurement. In a second step, the difference signal 110 between the active electrodes 120a-120n is measured. The pair of electrodes 120a-120n having the best difference signal 110 are selected for the following ECG measurement. This allows having the differential ECG derivation or lead which is similar to the first ECG derivation or lead in accordance with Einthoven. The electrode recognition routine may, depending on the system implementation, either remain active in the background of the measurement and permanently search for the best signal sources (electrodes 120a-120n with the best contact to the MC user or driver), or is only restarted after an interruption of the electrical or capacitively coupled contact to the MC user or driver.

Since there are certain linear dependencies between the individual standard derivations or leads of an ECG, it is possible, for example by combining several electrodes 120a-120n, to (partly) reconstruct a certain derivation or lead in compliance with the application, even though the actual measurement is not possible at that moment.

In other words, the electrode selecting device 140 monitors the electrode signals 130a-130n of the electrodes 120a-120n continuously and selects that pair of electrodes 120a-120n which provide the best difference signal 110 for determining the difference signal 110 based on the electrode signals 130a-130n.

Figure 4:
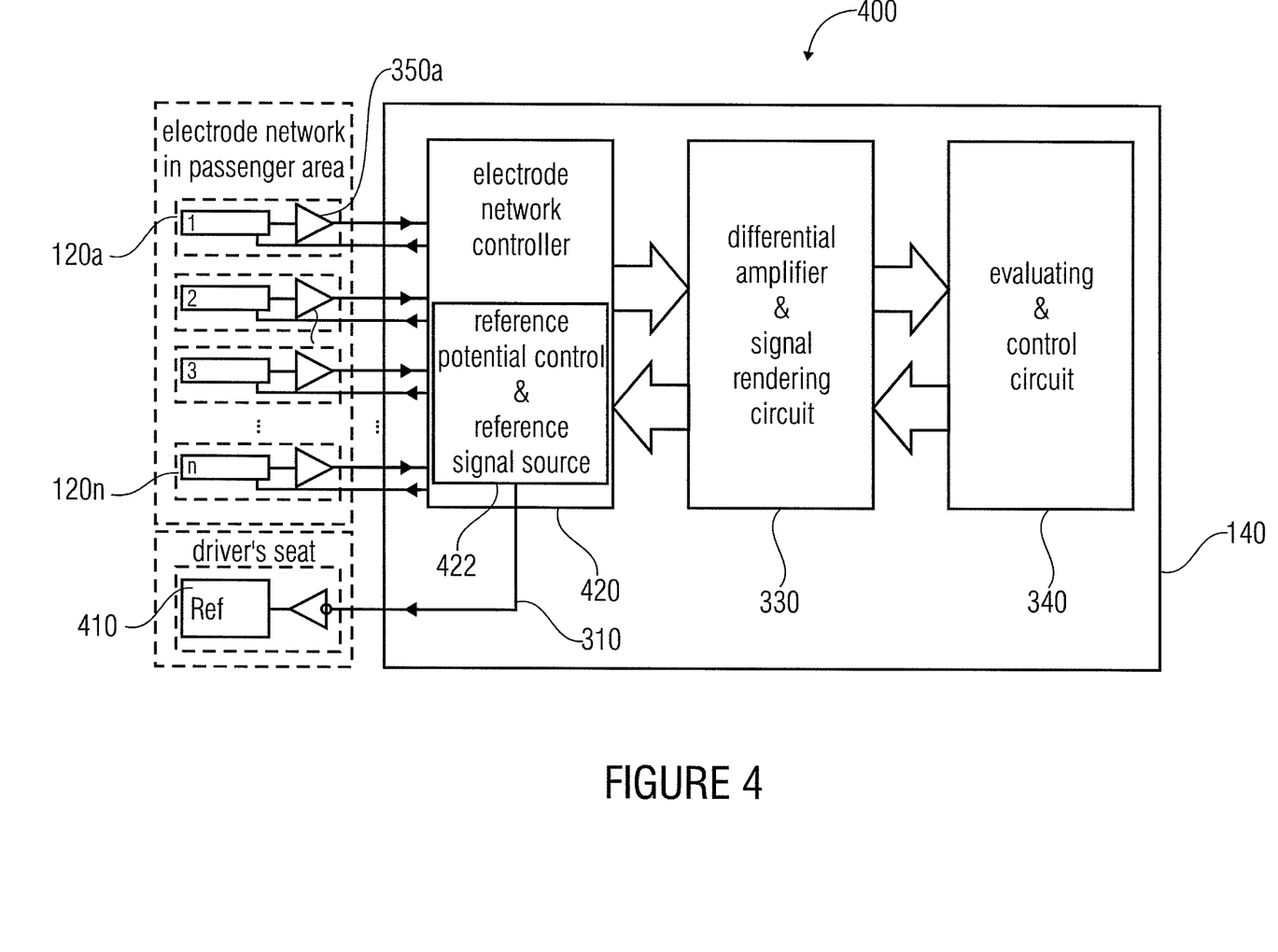
FIG. 4 shows a schematic illustration of a signal detecting device in accordance with a fourth embodiment of the present invention.

FIG. 4 shows a schematic illustration of a signal detecting device 400 in accordance with a fourth embodiment of the present invention. The signal detecting device 400 is configured to be integrated in an MC, for example, so as to exemplarily record an ECG of an MC user. The signal detecting device 400 includes an electrode network 120 of contact electrodes 120a-120n. An amplifier 350a-350n is connected downstream of each of the contact electrodes 120a-120n. An output of the amplifiers 350a-350n is each connected to an input of the electrode selecting device 140. The electrode selecting device 140 includes, in addition to the electrode network controller 420, a difference amplifier and signal rendering circuit 330 and an evaluating and control circuit 340. Additionally, the signal detecting device 400, in contrast to the signal detecting device 300, includes a reference electrode 410 which is, for example, integrated in a driver's seat of the MC. The reference electrode 410 is connected to a reference potential controller and reference signal source 422 of the electrode network controller 420.

In other words, FIG. 4 shows an exemplary integration of the signal detecting device 400 or the system for detecting the ECG by means of a network 120 of contract electrodes 120a-120n or capacitive electrodes 120a-120n, including a reference potential electrode 410 (which in medical technology is also referred to as "driven right leg" and serves reference potential control) in the driver's seat of the MC. The ECG electrodes 120a-120n are integrated in the passenger area of the MC. The large-area reference or reference potential electrode 410 for reference potential control and signal common-mode rejection is integrated in the driver's seat of the MC.

In addition to the solutions used as a standard for ECG detection, an additional reference signal 310 is fed to the MC user for electrode control (electrode recognition routine) via the reference electrode 410 in the driver's seat. This signal may be a DC signal, a sinusoidal signal or a modulated signal. The amplitude and frequency ranges of this reference signal 410 are in correspondence with the allowed threshold values for ECG measuring systems (for example patient leakage currents in accordance with ISO 60601). The pre-amplified signals from individual electrodes 120a-120n are detected using the comparator measuring system installed in the electrode network controller 420 of the electrode selecting device 140 and compared to the initial reference signal 310. The electrodes 120a-120n which are in contact with the MC user are determined by this and the electrodes 120a-120n exhibiting the best signal quality are selected on the basis of the signal intensity (exemplarily the portion of the electrode signals caused by the reference signal). Subsequently, the selected electrodes 120a-120n are fed to the differential amplifier 330 of the electrode selecting device 140 via a multiplexer matrix of different logical algorithms. Finally, the pair of ECG electrodes 120a-120n which have the best contact to the MC user and correspondingly provide the best difference signal 110 (or allow providing the best difference signal 110) is selected for detecting the ECG. The sum of the pre-amplified signals of both electrodes 120a-120n selected or the selected pair of electrodes 120a-120n is addition drained for the purpose of reference potential control before differential amplification and fed to the reference electrode 410 in the driver's seat of the MC. The reference signal 310 used for electrode detection (contact to the MC user, signal quality) will be filtered from the useful signal later on.

Figure 5:
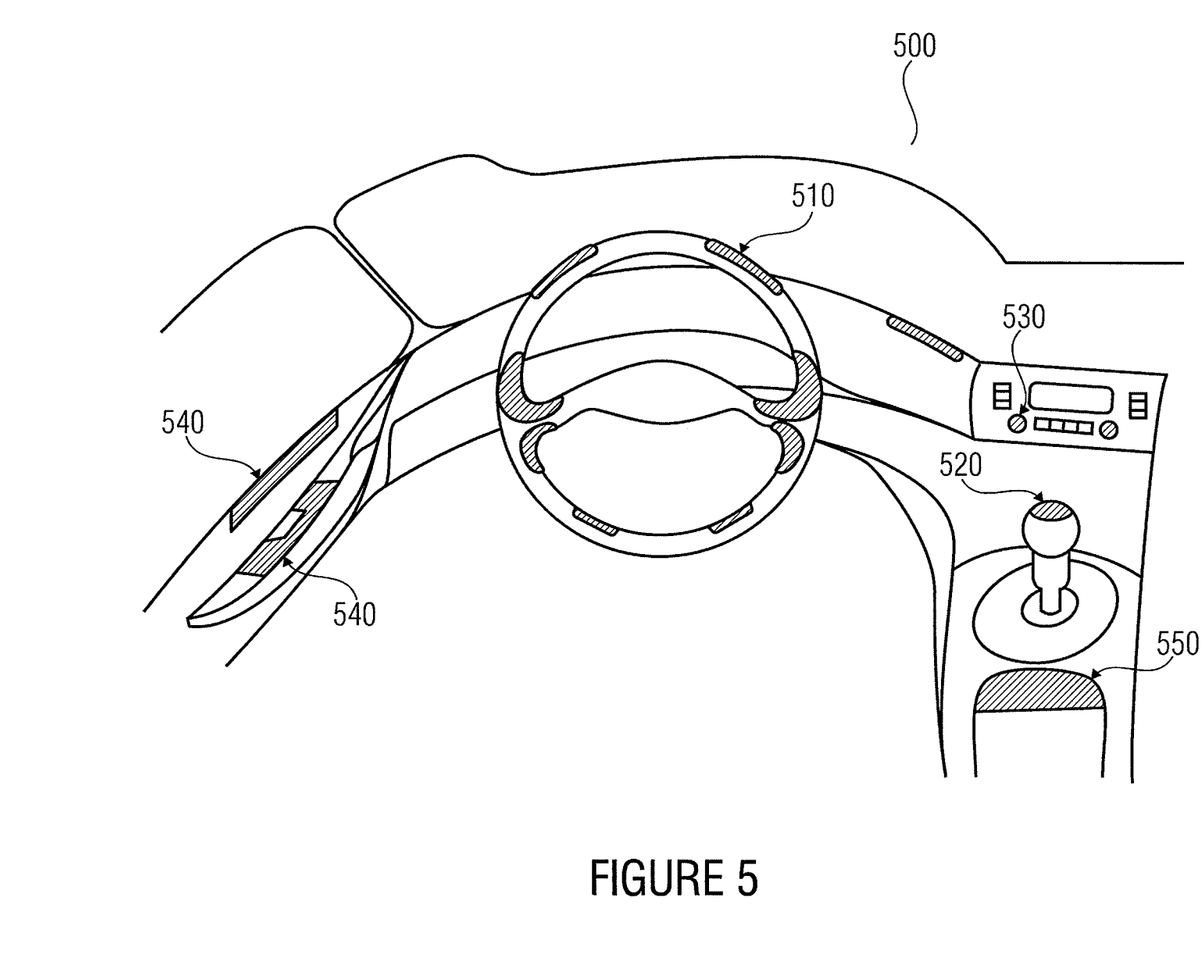
FIG. 5 shows a picture of an electrode arrangement in accordance with a fifth embodiment of the present invention.
Figure 7:
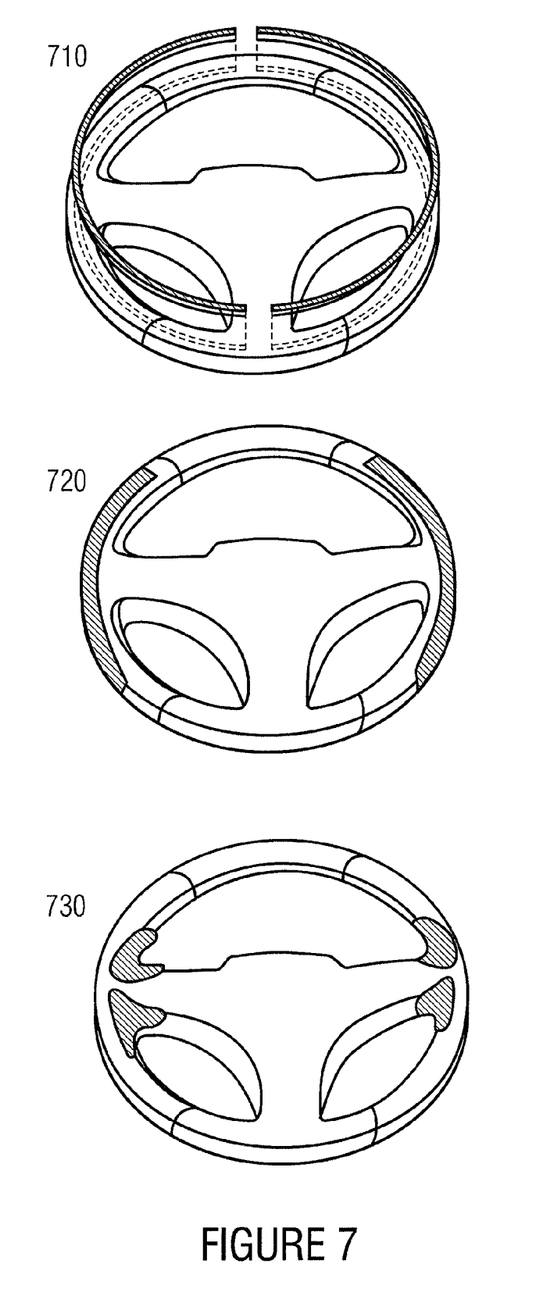
FIG. 7 shows a picture of an operating element for being used in an embodiment of the present invention.

FIG. 5 shows a picture of an electrode arrangement 500 in accordance with a fifth embodiment of the present invention. The electrodes of the electrode arrangement 500 in the fifth embodiment are integrated in different operating and rest elements of the MC. A steering wheel 510, an operating panel of a radio or a navigation apparatus 530 or a gear lever 520 are examples of operating elements of an MC. A door panel 540 or a central arm panel 550 are examples of rest elements. In the case of the steering wheel 510, the difference signals are detected when both hands of the driver rest on the steering wheel or touch the steering wheel. Electrodes are integrated in the steering wheel rim on the left and on the right. Three exemplary steering wheels 510 are shown in FIG. 7. The electrodes may exemplarily be implemented to be ring electrodes 710, area electrodes 720 or small-area electrodes 730 on the steering wheel 510. In the case of the gear lever 520, the difference signals can be detected when, for example, one hand is placed on the steering wheel 510 and the second hand on the gear lever 520, wherein the electrode for the ball of the thumb on the gear lever 520 may be integrated on the top side of the gear lever 520. In the case of the operating panel 530, difference signals can be detected when operating a navigation apparatus or radio (exemplarily when the other hand touches the steering wheel 510 at the same time or is placed on a rest).

Furthermore, rest elements may be used for detecting the difference signals. The door panel 540 can be used for detecting the difference signals when one hand of the MC user is exemplarily placed on the steering wheel 510 and the second hand of the MC user on the door panel 540. The armrest 550 may exemplarily be used for detecting the difference signals when one hand is placed on the steering wheel 510 and the second hand on the armrest 550. In addition, electrodes may also be integrated in other units of the MC which are contacted by the MC user, such as, for example, the driver's seat.

Since deriving an ECG is about detecting electrical potentials on the body of the driver, when integrating the electrodes into an MCs interior, the electrodes in the passenger area have to be integrated also taking potential sampling positions (control, operating, switching elements or elements of interior fittings of the MC which the driver while driving is to touch spontaneously as long and as frequency as possible), signal quality and security aspects into account.

Driver contacts to electrodes (touching electrode areas) are minimized above all by clothing and are mainly via the hands or palms. The electrode arrangement 500 shown in FIG. 5 is optimized for the highest probability of contacting to the MC user.

Figure 6:
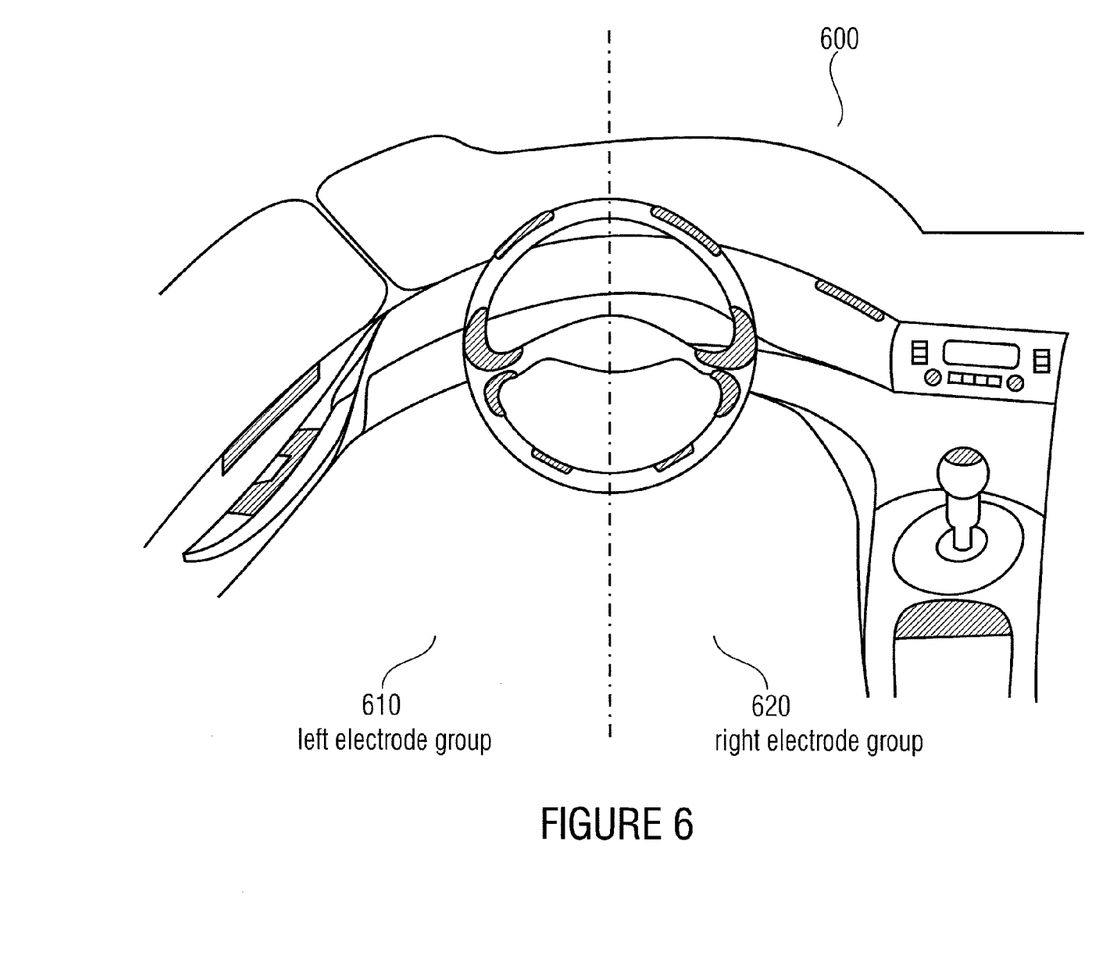
FIG. 6 shows a picture of an electrode arrangement in accordance with a sixth embodiment of the present invention.

One potential extension of the electrode arrangement 500 shown in FIG. 5 is illustrated in FIG. 6 as an electrode arrangement 600 in accordance with a sixth embodiment of the present invention. The ECG electrodes of the electrode arrangement in the passenger area may be subdivided into two groups for optimizing the electrode recognition routing. Electrodes which are mainly touched by the left hand or the left arm of the driver (i.e., for example, electrodes arranged to the left of the center of the driver's seat) are defined to be a left electrode group 6510 and electrodes which are mainly contacted by the right hand or right arm of the driver (i.e., exemplarily, electrodes arranged to the right of the center of the driver's seat) are defined to be a right electrode group 620.

The electrode arrangements 500 and 600 may exemplarily be implemented to be the electrode network 120 of the signal detecting device 300 described in FIG. 3.

Metallized plastic is an advantageous material for the electrodes mentioned in the first to sixth embodiments. Compared to solid full-metal electrodes, electrodes made of metallized plastics exhibit an improved temperature behavior. With direct insolation, metallic areas in the passenger area may heat up to more than 60° C., corresponding to the threshold of pain of human temperature sensitivity. In the case of electrodes made of metallized plastics, the plastic has the roll of a thermal insulator (i.e. acts as a thermal insulator) and additionally exhibits a considerably lower thermal capacity. The thin metal layer of these electrodes is heated strongly by environmental conditions, but does not store as much heat energy and quickly adapts same to body temperature when touched.

Using solid full-metal electrodes is not ruled out completely, these may be used in locations of favorable temperature conditions or where this seems to be appropriate for design reasons, such as, for example, as a race gear lever.

Alternatively, electrodes made of conductive plastics of different hardnesses (so-called "shore" factors) and conductivities, textile electrodes (such as, for example, in the form of thin metallic lines weaved into the cover fabric in the environment of the passenger area, for example, on the armrests) or capacitive electrodes may be used for recording an ECG in the vehicle.

Another embodiment of the present invention may be a system for detecting and continuously monitoring the ECG of a motorcar driver, train conductor, pilot etc. This system may either be used for medical care for cardiological patients, as a driver assistance system or for fostering a healthy life style (exemplarily as a so-called "lifestyle" product). The ECG allows drawing conclusions as to acute impairments (of, for example, the drivers performance) caused by stress, aggression or recognizing a dangerous situation, and chronic diseases manifesting themselves in rhythm disturbances or heart attacks. One embodiment of the present invention can be adapted to the environmental condition in a vehicle, such as, for example, a car. In particular, the sensors and measuring methods are recommended to fulfill to the following conditions: impairment of the driver is to be kept as small as possible, selecting the locations for mounting for sensor technology is done taking quality of the measuring values to be recorded and driver convenience into account, and when integrating sensor technology, security aspects (security-relevant units, such as, for example, steering wheel and hold back systems) in the MC or vehicle are to be taken into account.

In contrast to most known systems for monitoring drivers by means of vital sensor technology (such as, for example, ECG or pulse measurement), embodiments of the present invention take important aspects into consideration, such as, for example, signal quality, coverage of the passenger area with sensors, probability and frequency of the driver touching the sensors, and diversion of the driver caused by the interaction with the measuring system, and potentially, resulting impairments for driving security.

While typically detecting the ECG in an MC or vehicle is very difficult due to the challenging boundary conditions or lacking acceptance on the part of the driver, such as, for example, due to sensors placed on the body, an embodiment of the present invention allows detecting the ECG signals with a precision adapted to the respective case of application by integrating the sensors in operating and rest elements of an MC and the redundancy of the electrodes. Redundancy of the electrodes, as are exemplarily shown in FIGS. 5 to 7, in combination with a selection and processing of the electrode signals using the signal detecting device in accordance with FIGS. 3 and 4, for example, results in particularly good results since the redundancy of the electrodes, when using the signal detecting device, results in an improvement when determining the vital parameter.

The field of application for the invention is both in preventive, monitoring and accompanying medicine, and in the field of driver assistance and lifestyle applications (fitness coaching). One advantage of embodiments of the present invention is that the precision of recognizing the driver's state is improved significantly by using innovative sensors, ergonomic integration of the sensors into the vehicle's interior and, above all, detecting ECGs using redundant electrodes including following analysis and selection of the best signal source.

Another advantage is that one embodiment in accordance with the present invention exhibits considerably extended signal sampling possibilities and an enlarged total sampling area compared to known sensor arrangements for detecting a vital parameter. The vital parameters of the MC user can be detected with greater reliability than in other known systems, since the MC user contacts the sensor components with increased probability.

Another advantage is that applying the so-called application parts (parts which are conventionally fixed to the patients body, i.e., for example, electrodes) on the driver's body is not a prerequisite for measuring the vital parameters.

In addition, an MC user is not requested to get in contact with certain sensor elements while driving for the purpose of taking measurements. The measurements are taken in a way free of disturbances for the driver.

Furthermore, the system elements may be integrated into the interior and the operating elements of the vehicle such that they are hardly to be recognized from outside or integrated as design elements.

Although the embodiments shown of a signal detecting device and an electrode arrangement are configured to detect an ECG of a living being, it is also possible for further embodiments to be configured to detect other vital parameters, such as, for example, the pulse of a living being.

In summary, embodiments so the present invention allow implementing a method and a device which allow measurements of an ECG to be performed under automotive conditions at increased sensitivity and increased signal quality, without impairing the MC user. Thus, the ways of sampling the signal are extended considerably by using several redundant electrodes in the passenger area.

The method and devices described provide for integrating the devices (signal detecting device and electrode arrangement) for measuring the ECG in the elements of the interior (such as, for example, control elements, operating elements, switching elements etc.), which a driver contacts directly while driving.

Although embodiments of the present invention are implemented for being integrated into an MCs interior, there are further embodiments which are configured to be integrated in other vehicles which need continuous monitoring of vital parameters of the vehicle user. Airplanes, busses, etc. are examples of this.

The ECGs detected can optionally be settled, stored, analyzed and be illustrated directly for the MC user and/or the physician in charge (in the case of a medical case of application) and the result of the evaluation be illustrated suitably. When exceeding the adjustable threshold values of the vital parameters, a corresponding warning message or information message can be triggered.

It is additionally also possible for a specific driver profile with individual threshold values to be defined for each driver so as to eliminate inter-personal deviations. Subsequently, an individual performance profile (performance reserve) can be established using the driver's profile and the vital parameters detected. Using the performance profile, an optimum performance estimation for the driver can be performed depending on his health state (exemplarily an estimation of how long the driver is still able to drive without causing any danger for himself and for other road users, or how long a break should be).

The meaning of embodiments of the present invention in an MC or another means of transportation is supporting a driver or patient or warning the driver or patient and/or the physician in charge should the personal state established be a danger for the person itself or other road users. In the medium term, the system may optionally be developed further and may also be suitable for diagnosing.

Figure 8:
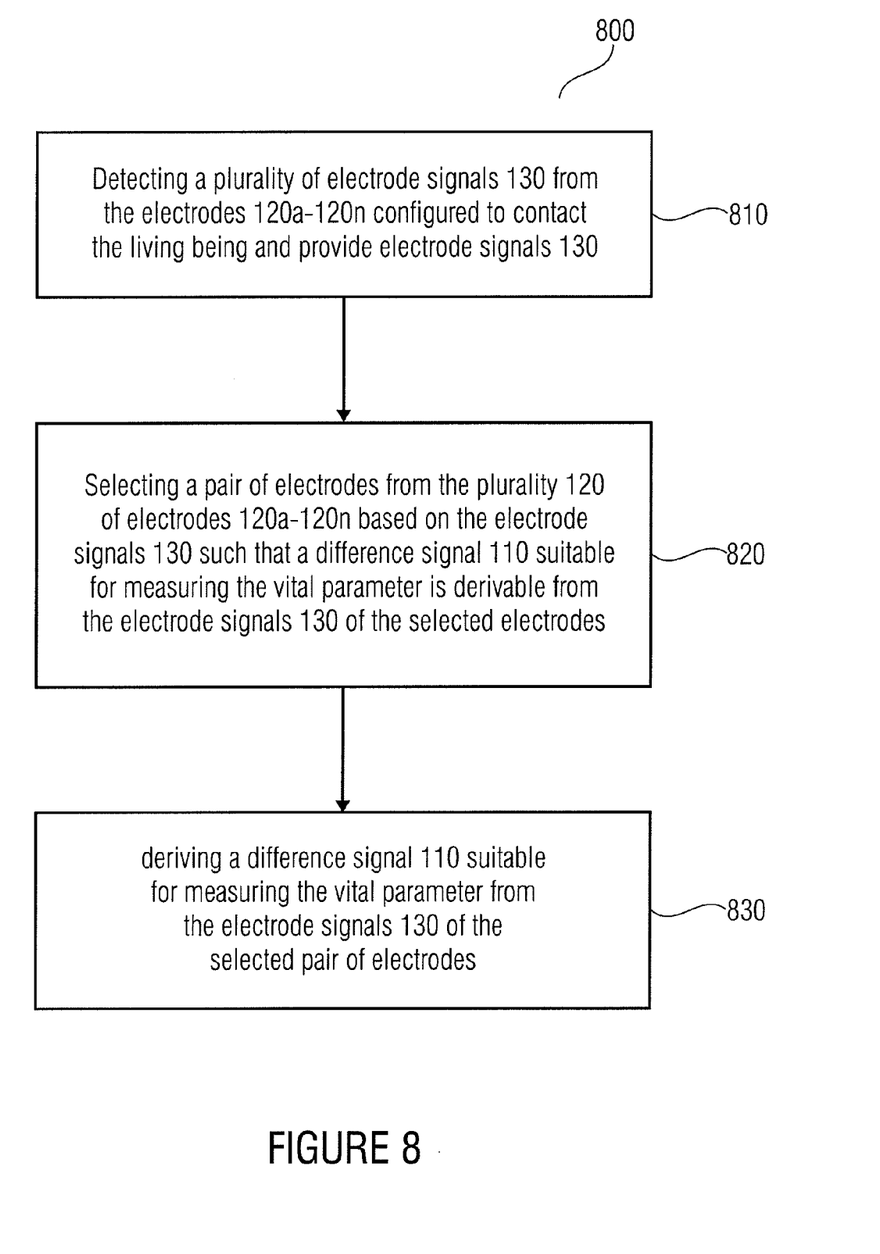
FIG. 8 shows a flowchart of a method in accordance with an embodiment of the present invention.

FIG. 8 shows a flowchart of a method 800 in accordance with an embodiment of the present invention. The method 800 for detecting a difference signal for electrically measuring a vital parameter of a living being using a plurality of electrode signals 130 from a plurality 120 of electrodes 120a to 120n includes a first step of detecting a plurality of electrode signals 130 from the electrodes 120a to 120n configured to contact the living being and provide electrode signals 130. Additionally, the method 800 includes a second step of selecting a pair of electrodes from the plurality 120 of electrodes 120a to 120n based on the electrode signals 130 so that a difference signal 110 suitable for measuring the vital parameter is derivable from the electrode signals 130 of the electrodes selected. Additionally, the method 800 includes a third step of deriving a difference signal 110 suitable for measuring the vital parameter from the electrode signals 130 of the selected pair of electrodes.

The method 800 may be supplemented by all the features and functionalities having been described with regard to the inventive devices.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. A signal detecting device for determining a difference signal for an electrical measurement of a vital parameter of a living being, comprising:
   a plurality of electrodes configured to contact the living being and provide electrode signals; and
   an electrode selecting device configured to select a pair of electrodes for determining the difference signal from the plurality of electrodes based on the electrode signals so that a difference signal suitable for measuring the vital parameter is derivable from the electrode signals of the selected electrodes;
   wherein the electrode selecting device is configured to:
      apply a reference signal to a first electrode from the plurality of electrodes, to detect an electrode signal at a second electrode from the plurality of electrodes, to decide, based on a signal strength of the electrode signal at the second electrode, whether the first electrode and the second electrode contact the living being sufficiently, and to select, responsive to a decision that the first electrode and the second electrode contact the living being sufficiently well, the first electrode and the second electrode as the pair of electrodes for determining the difference signal, or to mark the first electrode and the second electrode as candidate electrodes for the selection of the pair of electrodes for determining the difference signal.

2. The signal detecting device in accordance with claim 1, wherein the electrode selecting device is configured to detect signals provided by individual electrodes from the plurality of electrodes and compare these signals to a reference signal or several reference signals so as to establish electrodes which are in electrically or capacitively coupled contact to the living being and enable same for a measurement of the difference signal.

3. The signal detecting device in accordance with claim 1, wherein the electrode selecting device is configured to compare, when selecting a pair of electrodes for measuring the vital parameter, a first difference signal of a first pair of electrodes from the plurality of electrodes to a second difference signal of a second pair of electrodes from the plurality of electrodes, and to select that pair of electrodes for determining the difference signal for the electrical measurement of the vital parameter, comprising, when selecting, the greatest difference signal.

4. The signal detecting device in accordance with claim 1, wherein the electrode selecting device is configured to apply a reference signal to a first electrode from the plurality of electrodes so as to detect an electrode signal at a second electrode from the plurality of electrodes, and to decide, based on a signal strength of the electrode signal at the second electrode, whether the first electrode and the second electrode contact the living being sufficiently, and to, responsive to a decision that the first electrode and the second electrode contact the living being sufficiently well, mark the first electrode and the second electrode as a candidate pair for the selection of the pair of electrodes for determining the difference signal for the electrical measurement of the vital parameters, and to compare the difference signals of a plurality of candidate pairs to select that candidate pair from the plurality of candidate pairs as pair of electrodes for determining the difference signal for the electrical measurement of the vital parameter, which exhibit a greatest difference signal based on the comparison.

5. The signal detecting device in accordance with claim 4, wherein the electrode selecting device is configured to perform establishing the candidate pairs which contact the living being based on a search algorithm, wherein the electrode selecting device is configured to iteratively apply a reference signal to mutually different reference electrodes from the plurality of electrodes and to detect an electrode signal from at least one non-reference electrode from the plurality of electrodes.

6. The signal detecting device in accordance with claim 1, further comprising a reference electrode, wherein the electrode selecting device is configured to apply a reference potential and/or a reference signal to the reference electrode and to leave the reference electrode unconsidered when selecting the pair of electrodes for determining the difference signal.

7. The signal detecting device in accordance with claim 1, further comprising a storage device configured to detect a duration of contacting of the electrodes from the plurality of electrodes to the living being, and to derive a contacting probability of the electrodes based on the duration of the contacting of the electrodes to the living being.

8. The signal detecting device in accordance with claim 1, wherein the plurality of electrodes are arranged in a motorcar (MC) so as to contact an MC user;

wherein at least a first electrode from the plurality of electrodes is arranged at or in an operating element of the MC; and wherein at least a second electrode from the plurality of electrodes is arranged at or in a rest element of the MC.

9. The signal detecting device in accordance with claim 8, wherein the plurality of electrodes comprise a first group of electrodes and a second group of electrodes;

wherein the first group of electrodes is associated to a first body half of the MC user;

wherein the second group of electrodes is associated to a second body half of the MC user;

wherein the first group of electrodes is arranged to contact the first body half of the MC user; and wherein the second group of electrodes is arranged to contact the second body half of the MC user; and wherein the electrode selecting device is configured to select the pair of electrodes for determining the difference signal for the electrical measurement of a vital parameter such that a first electrode of the pair is from the first group of electrodes and a second electrode of the pair is from the second group of electrodes.

10. An electrode arrangement comprising: a plurality of electrodes; and an electrode selecting device configured to select a pair of electrodes for determining a difference signal from the plurality of electrodes based on the electrode signals so that a difference signal suitable for measuring a vital parameter of a living being is derivable from the electrode signals of the selected electrodes;

wherein the electrode selecting device is configured to: apply a reference signal to a first electrode from the plurality of electrodes, to detect an electrode signal at a second electrode from the plurality of electrodes, to decide, based on a signal strength of the electrode signal at the second electrode, whether the first electrode and the second electrode contact the living being sufficiently, to select, responsive to a decision that the first electrode and the second electrode contact the living being sufficiently well, the first electrode and the second electrode as the pair of electrodes for determining the difference signal, or to mark the first electrode and the second electrode as candidate electrodes for the selection of the pair of electrodes for determining the difference signal;

wherein the plurality of electrodes are arranged in a motorcar (MC) so as to contact an MC user;

wherein at least the first electrode from the plurality of electrodes is arranged at or in an operating element of the MC;

wherein at least the second electrode from the plurality of electrodes is arranged at or in a rest element of the MC; and wherein the rest element is an armrest area, a door panel or a central arm panel.

11. The electrode arrangement in accordance with claim 10, wherein the first electrode from the plurality of electrodes is arranged so as to contact a first hand or a first arm of the MC user; and wherein the second electrode from the plurality of electrodes is arranged so as to contact a second hand or a second arm of the MC user.

12. The electrode arrangement in accordance with claim 10, further comprising a reference electrode, the reference electrode being arranged in a driver's seat of the MC so as to couple the MC user capacitively.

13. The electrode arrangement in accordance with claim 10, wherein at least a third electrode from the plurality of electrodes is arranged at or in a security element of the MC.

14. The electrode arrangement in accordance with claim 10, wherein at least one electrode from the plurality of electrodes comprises a metallized plastic layer.

15. The electrode arrangement in accordance with claim 10, wherein at least one electrode from the plurality of electrodes comprises a layer made of conductive plastic.

16. The electrode arrangement in accordance with claim 10, wherein at least one electrode from the plurality of electrodes is implemented to be a textile electrode.

17. The electrode arrangement in accordance with claim 10, wherein at least one of the electrodes from the plurality of electrodes is implemented to be a capacitive electrode so as to couple the MC user capacitively.

18. A method for determining a difference signal for an electrical measurement of a vital parameter of a living being using a plurality of electrode signals from a plurality of electrodes, comprising:

a) detecting a plurality of electrode signals from the electrodes configured to contact the living being and provide electrode signals;

b) selecting a pair of electrodes from the plurality of electrodes based on the electrode signals such that a difference signal suitable for measuring the vital parameter is derivable from the electrode signals of the selected electrodes;

c) deriving a difference signal suitable for measuring the vital parameter from the electrode signals of the selected pair of electrodes;

d) applying a reference signal to a first electrode from the plurality of electrodes;

e) detecting an electrode signal at a second electrode from the plurality of electrodes;

f) deciding, based on a signal strength of the electrode signal at the second electrode, whether the first electrode and the second electrode contact the living being sufficiently; and g) selecting, responsive to a decision that the first electrode and the second electrode contact the living being sufficiently well, the first electrode and the second electrode as the pair of electrodes for determining the difference signal, or to mark the first electrode and the second electrode as candidate electrodes for the selection of the pair of electrodes for determining the difference signal.

19. A signal detecting device for determining a difference signal for an electrical measurement of a vital parameter of a living being, comprising:

a plurality of electrodes configured to contact the living being and provide electrode signals; and an electrode selecting device configured to select a pair of electrodes for determining the difference signal from the plurality of electrodes based on the electrode signals so that a difference signal suitable for measuring the vital parameter is derivable from the electrode signals of the selected electrodes;

wherein the electrode selecting device is configured to compare, when selecting a pair of electrodes for measuring the vital parameter, a first difference signal of a first pair of electrodes from the plurality of electrodes to a second difference signal of a second pair of electrodes from the plurality of electrodes, and to select that pair of electrodes for determining the difference signal for the electrical measurement of the vital parameter, comprising, when selecting, the greatest difference signal.

* * * * *

UNITED STATES PATENT AND TRADEMARK OFFICE
CERTIFICATE OF CORRECTION

| | | |
|---|---|---|
| PATENT NO. | : 8,847,769 B2 | Page 1 of 1 |
| APPLICATION NO. | : 12/913566 | |
| DATED | : September 30, 2014 | |
| INVENTOR(S) | : Ershov | |

It is certified that error appears in the above-identified patent and that said Letters Patent is hereby corrected as shown below:

On the title page, item [54] and in the specification, column 1, line 1-5, Title: "SIGNAL DETECTING DEVICE FOR DETECTING A DIFFERENCE SIGNAL FOR AN ELECTRICAL MEASUREMENT OF A VITAL PARAMETER OF A LIVING BEING" should read --SIGNAL DETECTING DEVICE FOR DETECTING A DIFFERENCE SIGNAL FOR AN ELECTRICAL MEASUREMENT OF A VITAL PARAMETER OF A LIVING BEING, ELECTRODE ARRANGEMENT AND METHOD--

Signed and Sealed this
Twenty-third Day of February, 2016

Michelle K. Lee
*Director of the United States Patent and Trademark Office*